United States Patent [19]

Bourson et al.

[11] Patent Number: 5,962,472

[45] Date of Patent: Oct. 5, 1999

[54] USE OF 4-PHENYL-3,6-DIHYDRO-2H-PYRIDYL DERIVATIVES

[75] Inventors: Anne Bourson, Mulhouse, France; Günther Fischer, Lörrach-Brombach, Germany; Marie-Paule Heitz Neidhart, Hagenthal le Bas; Vincent Mutel, Mulhouse, both of France; Gerhard Trube, Rheinfelden, Germany

[73] Assignee: Hoffmann-La Roche Inc., Nutley, N.J.

[21] Appl. No.: 08/813,523

[22] Filed: Mar. 7, 1997

[30] Foreign Application Priority Data

Mar. 8, 1996 [EP] European Pat. Off. .............. 96103636

[51] Int. Cl.[6] ..................................................... A01N 43/40
[52] U.S. Cl. ............................................. 514/317; 514/277
[58] Field of Search ...................... 514/317, 277

[56] References Cited

U.S. PATENT DOCUMENTS

| | | | |
|---|---|---|---|
| 3,674,799 | 7/1972 | Edenhofer et al. | 260/294.8 |
| 3,723,445 | 3/1973 | Edenhofer et al. | 260/295 |
| 3,879,405 | 4/1975 | Edenhofer | 260/294.8 |

FOREIGN PATENT DOCUMENTS

| | | |
|---|---|---|
| 445701 | 9/1991 | Japan . |
| 9502431 | 3/1995 | South Africa . |
| WO 96/41629 | 12/1996 | Switzerland . |

OTHER PUBLICATIONS

European Journal of Pharm. vol. 187 No. 3, pp. 513–518, 1990.
Journ. of Med. Chem. vol. 31, No. 8, pp. 1621–1625, 1988.
Expert Opinion on Investigational Drugs, vol. 3, No. 4, pp. 341–354, 1994.
Indian Journal of Chemistry, vol. 15B pp. 466–472, 1977.
Abstract corresponding to DE 43 25855.
R. W. Ransom & N. L Stec. Journal of Neurochemistry 51, pp. 830–836 (1988).
Hollmann & Heinemann, 1994, Annu, Rev. Neurosci. 17:31–108.
Malherbe et al., 1990, Mol. Brain Res. 8:199.
Abstract corresponding to FR 2681319.

*Primary Examiner*—Dwayne C. Jones
*Attorney, Agent, or Firm*—George W. Johnston; Patricia S. Rocha-Tramaloni; Alan P. Kass

[57] ABSTRACT

The present invention relates to the use of compounds of general formula

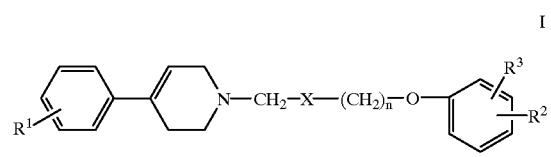

wherein
$R^1$ is hydrogen, halogen, lower alkyl or lower alkoxy;
$R^2$ is hydrogen;
$R^3$ is hydrogen, amino, ureido, lower alkylcarbonyl, lower alkyl-sulfonylamino, lower alkylcarbamoyl, carbamoyl, lower alkyloxycarbamoyl, lower alkylamino or
$R^2$ and $R^3$ taken together are $-(CH_2)_m-$
X is methylene, hydroxymethylene, lower alkoxymethylene or carbonyl,
n is 0, 1 or 2 and
m is 3 or 4
as well as pharmaceutically acceptable salts for the control or treatment of diseases which represent therapeutic indications for NMDA receptor subtype specific blockers.

12 Claims, No Drawings

USE OF 4-PHENYL-3,6-DIHYDRO-2H-PYRIDYL DERIVATIVES

BRIEF SUMMARY OF THE INVENTION

The invention relates to compounds of the formula

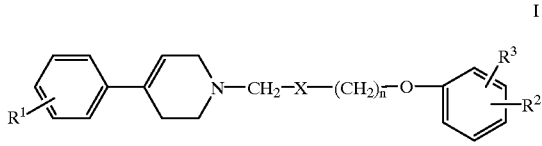

wherein
$R^1$ is hydrogen, halogen, lower alkyl or lower alkoxy;
$R^2$ is hydrogen;
$R^3$ is hydrogen, amino, ureido, lower alkylcarbonyl, lower alkyl-sulfonylamino, lower alkylcarbamoyl, carbamoyl, lower alkyloxycarbamoyl, lower alkylamino or
$R^2$ and $R^3$ taken together are —$(CH_2)_m$—
X is methylene, hydroxymethylene, lower alkoxymethylene or carbonyl,
n is 0, 1 or 2 and
m is 3 or 4
or pharmaceutically acceptable salts thereof and their use as NMDA-receptor subtype selective blockers.

DETAILED DESCRIPTION OF THE INVENTION

The invention relates to compounds of the formula

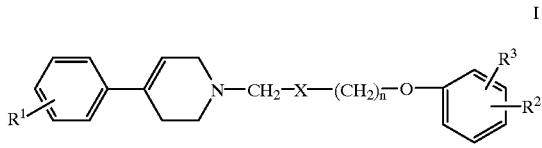

wherein
$R^1$ is hydrogen, halogen, lower alkyl or lower alkoxy;
$R^2$ is hydrogen;
$R^3$ is hydrogen, amino, ureido, lower alkylcarbonyl, lower alkyl-sulfonylamino, lower alkylcarbamoyl, carbamoyl, lower alkyloxycarbamoyl, lower alkylamino or
$R^2$ and $R^3$ taken together are —$(CH_2)_m$—
X is methylene, hydroxymethylene, lower alkoxymethylene or carbonyl,
n is 0, 1 or 2 and
m is 3 or 4
or pharmaceutically acceptable salts thereof and their use as NMDA-receptor subtype selective blockers.

The above described compounds and their salts are known compounds. In U.S. Pat. No. 3,723,445 and DE 1 964 421 these compounds are stated to possess antiphlogistic, antiallergic, antitussive and analgesic properties.

It has now surprisingly been found that compounds of the present invention are NMDA-receptor subtype selective blockers.

NMDA receptors have a key function in modulating neuronal activity and plasticity which makes them key players in mediating processes underlying development of CNS as well as learning and memory formation. Under pathological conditions of acute and chronic forms of neurodegeneration overactivation of NMDA receptors is a key event for triggering neuronal cell death.

NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors, displaying different pharmacological properties.

Therapeutic indications for NMDA receptor subtype specific blockers include acute forms of neurodegeneration caused, for example, by stroke and brain trauma, and chronic forms of neurodegeneration such as Alzheimer's disease, Parkinson's disease, Huntington's disease, ALS (amyotrophic laterial sclerosis) and neurodegeneration associated with bacterial or viral infections.

Compounds of the present invention are therefore useful in the treatment of acute forms of neurodegeneration caused, for example, by stroke and brain trauma, and chronic forms of neurodegeneration such as Alzheimer's disease, Parkinson's disease, Huntington's disease, ALS (amyotrophic laterial sclerosis) and neurodegeneration associated with bacterial or viral infections.

Objects of the present invention are the use of compounds of formula I in the treatment or prophylaxis of diseases caused by overactivation of respective NMDA receptor subtypes, such as acute forms of neurodegeneration caused, for example, by stroke and brain trauma, and chronic forms of neurodegeneration such as Alzheimer's disease, Parkinson's disease, Huntington's disease, ALS (amyotrophic laterial sclerosis) and neurodegeneration associated with bacterial or viral infections, the use of these compounds for manufacture of corresponding medicaments, and medicaments containing these compounds.

In another aspect, the present invention relates to a method of reducing acute or chronic forms of neurodegeneration which comprises administering to a host in need of such treatment an effective amount of a compound of formula I.

The following definitions of the general terms used in the present description apply irrespective of whether the terms in question appear alone or in combination.

As used herein, the term "lower alkyl" denotes a straight or branched-chain alkyl group containing from 1 to 4 carbon atoms, for example, methyl, ethyl, propyl, isopropyl, butyl and the like.

The term "halogen" denotes chlorine, iodine, fluorine or bromine. The term "lower alkoxy" denotes an alkyl group, as defined earlier which is attached via an oxygen atom.

The term "carbamoyl" denotes the group —$NH_2CO$—.

The term "hydroxymethylene" denotes the group —CH(OH)— and "alkoxymethylene" denotes the group —CH(alkoxy)—.

The compounds of formula I, in which X represents a hydroxy-methylene or lower alkoxymethylene contain one asymmetric carbon atom. Accordingly, the formation of two enantiomers is possible. The present invention embraces racemic mixtures and their corresponding enantiomers.

Exemplary preferred compounds are:
[4-[3-[4-(4-Fluoro-phenyl)-3,6-dihydro-2H-pyridin-1-yl]-2-hydroxy-propoxy]-phenyl]-urea,
N-[4-[3-[4-(4-Fluoro-phenyl)-3,6-dihydro-2H-pyridin-1-yl]-propoxy]-phenyl]-methanesulfonamide hydrochloride (1:1),
N-[4-[3-[4-(4-Fluoro-phenyl)-3,6-dihydro-2H-pyridin-1-yl]-2-hydroxy-propoxy]-phenyl]-methanesulfonamide,
[4-[3-[4-(4-Fluoro-phenyl)-3,6-dihydro-2H-pyridin-1-yl]-2-hydroxy-propoxy]-phenyl]-carbamic acid ethyl ester,
N-[4-[3-[4-(4-chloro-phenyl)-3,6-dihydro-2H-pyridin-1-yl]-propoxy]-phenyl]-acetamide and N-[4-[2-[4-(4-Fluoro-phenyl)-3,6-dihydro-2H-pyridin-1-yl]-ethoxy]-phenyl]-methanesulfonamide.

The compounds of formula I and their pharmaceutically acceptable salts can be prepared by processes, described in the above mentioned references. For example, DE 1 964 421 describes a process which comprises reacting a compound of the formula

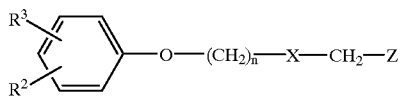

wherein $R^2$, $R^3$ and X are as described above and Z is a leaving group, such as halogen,
with a compound of the formula

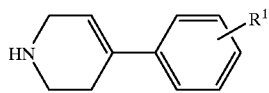

wherein $R^1$ is as described above.

A further process is described in U.S. Pat. No. 3,723,445 which process comprises reacting a compound of the formula

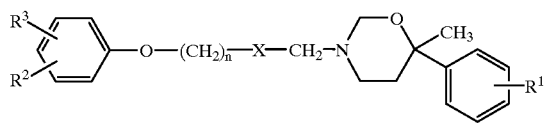

wherein $R^1$, $R^2$, $R^3$, X and n are described above, with a mineral acid, such as concentrated hydrochloric acid.

As described above, the compounds of formula I can contain one asymmetric carbon atoms and the formation of two enantioners is possible. The racemates can, if desired, be separated into their optical antipodes by known methods, for example, by fractional crystallization of the salts with optically active acids, such as α-tartaric acid, dibenzoyl-α-tartaric acid or α-camphorsulfonic acid.

The compounds of formula I can be converted into pharmaceutically acceptable acid addition salts. These salts can be manufactured according to known methods which will be familiar to any person skilled in the art.

The activity of compounds of formula I can be demonstrated by the following:

3H-MK801 (Dizocilpine) binding in vitro

The whole brain from 150–200 g male rats, without cerebellum and without medulla oblongata was dissected on ice. The tissue was then homogenized with an Ultra-Turrax maximum speed during 30 seconds at 4° C. in 50 volumes of cold Tris HCl 50 mM, EDTA disodium 10 mM, pH=7.4 buffer (wet weight/v). The homogenate was centrifuged at 48'000 x g (20'000 rpm, SS34, Sorvall RC5C) for 10 minutes. The pellet was rehomogenized with the same volume of buffer and the homogenate incubated at 37° C. for 10 minutes. After centrifugation as above, the pellet was rehomogenized with the same volume of buffer and frozen at −80° C. in 35 ml fractions for at least 16 hours and not more than 2 weeks.

For the binding experiment, the homogenate was centrifuged as above and the pellet was washed 3 times by homogenization in 25 volumes of cold Tris HCl 5mM, pH=7.4 buffer (Ultra-Turrax, maximum speed, 30 seconds) and centrifugation as above. The final pellet was rehomogenized in 25 volumes of buffer (original wet weight) and used as such in the assay. The final concentration of membrane in the assay was 20 mg/ml (wet weight).

The incubation was performed in the presence of 1 nM glutamate, glycine and spermidine. MK-801, (+)-[3-3H(N)], NEN (NET-972) 20Ci/mmol, was used at 5 nM final concentration. Non specific binding was determined in presence of 100NM 1-[1-(2-Thienyl)cyclohexyl]piperidine (TCP). After 2 hours of incubation at room temperature, the suspension was filtered (Whatmann GF/B, soaked in 0.1% polyethylenimine for 2 hours) and washed 5 times with 3 ml of cold Tris HCl 5mM, pH=7.4 buffer. The air-dried filters were counted with 10 ml of Ultima-gold (Packard) in a Tri-Carb 2500 TR scintillation counter after agitation.

The radioactive decays per minute (DPM) were transformed in % of specific binding and these values were treated by a non linear regression calculation program (BINDING, H. Affolter, Switzerland) which provided the $IC_{50}$ values for the low and high affinity binding sites (=concentrations producing half maximal inhibition at the respective sites). Each experiment was repeated at least three times and the final $IC_{50}$ values were calculated as the mean +/−standard deviation of the individual experiments.

Reference: R. W. Ransom and N. L. Stec. Journal of Neurochemistry 51, 830–836, 1988.

Electrophysiology on recombinant NMDA receptors cDNA clones coding for the subunits NMDAR1C and NMDAR2A of the NMDA receptor (see Hollmann and Heinemann, 1994, Annu. Rev. Neurosci. 17:31 for nomenclature of NMDA receptor subunits) were isolated from a rat brain λgt11 cDNA library as published elsewhere (Sigel et al., 1994, J. Biol. Chem. 269:8204). The clone for the subunit NMDAR2B of the rat brain NMDA receptor was obtained from S. Nakanishi (Kyoto, Japan). The cDNAs were transcribed, capped and poly(A+)-tailed as described previously (Malherbe et al., 1990, Mol. Brain Res. 8: 199). Oocytes of South African frogs (Xenopus laevis) were used for expressing either a combination of the NMDAR1C and NMDAR2A subunits or the NMDAR1C and NMDAR2B subunits. Approximately 3 fmol of a 1:1 mixture of the respective mRNA species were injected into every oocyte. Four to five days later the ion current through the NMDA receptor channels was measured in voltage clamp experiments (see Methfessel et al., 1986, Pfliigers Arch. 407:577 for the methods of oocyte expression and voltage-clamping). The membrane potential was clamped to −80 mV and the receptors were activated by applying a modified Ringer's solution containing the NMDA-receptor agonists L-asparatate (Asp) and glycine (Gly). Different agonist concentrations were chosen for either subunit combination to account for the different agonist sensitivities of the two types of receptors (70 μM Asp plus 2.5 μM Gly for NMDAR1C—NMDAR2A and 15 μM Asp plus 0.2 μM Gly for NMDAR1C—NMDAR2B). The agonists were applied for 15 s intervals once every 2.5 min by rapid superfusion of the oocyte with agonist containing solution and the amplitude of the agonist-evoked current was measured immediately before the end of each application. After a series of initial control applications, increasing concentrations of the antagonist to be tested were added to both, the basal Ringer's and the agonist containing solution. The antagonist concentration was usually increased in decade steps and the oocyte was exposed to any concentration for at least 5 min. For the data analysis the amplitude (y) of the agonist-induced current was plotted versus the concentration (x) of the antagonist and the logistic function $y=A/[1+(x/IC_{50})H]$ was fitted to the data to estimate the 50% inhibitory concentration ($IC_{50}$). Three to six oocytes were tested for every antagonist and, if possible, at least 3 concentrations embracing the $IC_{50}$ were applied to every oocyte. However, in the case of the NMDAR1C plus NMDAR2A subunit combination 50% inhibition was not reached at the solubility limit of the compounds (20–30 $\mu$M). In this case the highest tested concentration preceded by a "larger" sign (">") is given in the table "Test Results". Figures for the $IC_{50}$ in all other cases are arithmetic mean values of individual $IC_{50}$s determined by the logistic curve fits.

Tested compounds of formula I

| $R^1$ | $R^2$ | $R^3$ | X | n | compound No. |
|---|---|---|---|---|---|
| p-F | H | p-NH—CO—NH$_2$ | —CH(OH)— | 1 | A |
| p-F | H | p-NHSO$_2$CH$_3$ | —CH$_2$— | 1 | B |
| p-F | H | p-NHSO$_2$CH$_3$ | —CH(OH)— | 1 | C |
| p-F | H | p-NHCOOC$_2$H$_5$ | —CH(OH)— | 1 | D |
| p-Cl | H | p-NHCOCH$_3$ | —CH$_2$— | 1 | E |
| p-F | H | p-NHCOCH$_3$ | —CH$_2$— | 1 | F |
| p-F | H | p-NHSO$_2$CH$_3$ | —CH$_2$— | 0 | G |
| p-F | H | p-CONH$_2$ | —CH(OH)— | 1 | H |
| H | H | p-NHCOCH$_3$ | —CH(OH)— | 1 | I |
| p-F | H | p-NH$_2$ | —CH$_2$— | 1 | j |
| p-OCH$_3$ | H | p-NHCOCH$_3$ | —CH$_2$— | 1 | k |
| p-F | H | p-NHCOC$_2$H$_5$ | —CH$_2$— | 1 | l |
| H | H | H | —CH(OH)— | 1 | M |
| p-F | together —(CH$_2$)$_3$— | | —CH(OH)— | 1 | N |
| H | H | p-COCH$_3$ | CH$_2$— | 1 | O |

Test results

| | $^3$H-MK801/IC$_{50}$ ($\mu$M) | | Electrophysiology/IC$_{50}$ ($\mu$M) | |
|---|---|---|---|---|
| compound No. | high | low | NMDAR 1C u. 2A | NMDAR 1C u. 2B |
| A | 0.02 | 55 | | |
| B | 0.02 | 75 | | |
| C | 0.02 | 69 | | |
| D | 0.136 | 320 | >20 | 0.63 |
| E | 0.2 | 88 | | |
| F | 0.2 | 85 | | |
| G | 0.236 | 24 | >30 | 0.80 |
| H | 0.33 | 40 | >30 | 0.71 |
| I | 0.41 | 110 | | |
| J | 0.78 | 44 | | |
| K | 0.91 | 76 | | |
| L | 1.00 | 110 | | |
| M | 1.75 | 102 | | |
| N | 1.96 | 258 | | |
| O | 7.5 | 298 | | |

By screening, compounds of formula I could be identified as NMDA receptor subtype selective blockers. For selected compounds, the preference for NMDAR-2B subunits could be demonstrated by electrophysiological characterization using cloned NMDA receptor subtypes expressed in oocytes.

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The daily dose of compounds of formula I to be administered varies with the particular compound employed, the chosen route of administration and the recipient. Representative of a method for administering the compounds of formula I is by the oral and parenteral type administration route. An oral formulation of a compound of formula I is preferably administered to a human adult at a dose in the range of 500 mg to 1.5 gm per day. A parenteral formulation of a compound of formula I is preferably administered to a human adult at a dose in the range of 5 to 1000 mg per day. An average human adult weighs 70 kg.

The invention is further illustrated in the following examples.

EXAMPLE 1
Tablet Formulation (Wet Granulation)

| | mg / tablet | | | |
|---|---|---|---|---|
| Item Ingredients | 5 mg | 25 mg | 100 mg | 500 mg |
| 1. Compound of formula I | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| TOTAL | 167 | 167 | 167 | 835 |

Manufacturing Procedure:

1. Mix Items 1, 2, 3 and 4 and granulate with purified water.

2. Dry the granulation at 50° C.

3. Pass the granulation through suitable milling equipment.

4. Add Item 5 and mix for three minutes; compress on a suitable press.

EXAMPLE 2
Capsule Formulation

| | mg / capsule | | | |
|---|---|---|---|---|
| Item Ingredients | 5 mg | 25 mg | 100 mg | 500 mg |
| 1. Compound of formula I | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| TOTAL | 200 | 200 | 300 | 600 |

Manufacturing Procedure

1. Mix Items 1, 2, and 3 in a suitable mixer for 30 minutes.

2. Add Items 4 and 5 and mix for 3 minutes.

3. Fill into a suitable capsule.

EXAMPLE 3
Tablet Formulation (Wet Granulation)

|  | mg / tablet | | | |
|---|---|---|---|---|
| Item Ingredients | 5 mg | 25 mg | 100 mg | 500 mg |
| 1. Compound of formula I | 5 | 25 | 100 | 500 |
| 2. Lactose Anhydrous | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 2 | 2 | 5 |
| TOTAL | 167 | 167 | 167 | 835 |

Manufacturing Procedure

1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

We claim:

1. A method for the control or treatment of diseases caused by over activation of NMDA receptor subtypes comprising orally administering to a host in need of such control or treatment, a compound of the formula

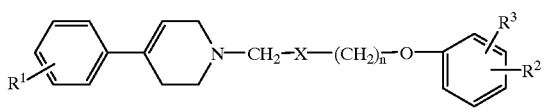

wherein
$R^1$ is hydrogen, halogen, lower alkyl or lower alkoxy;
$R^2$ is hydrogen;
$R^3$ is hydrogen, amino, ureido, lower alkylcarbonyl, lower alkyl-sulfonylamino, lower alkylcarbamoyl, carbamoyl, lower alkyloxycarbamoyl, lower alkylamino or
$R^2$ and $R^3$ taken together are —$(CH_2)_m$—;
X is methylene, hydroxymethylene, lower alkoxymethylene or carbonyl;
n is 0, 1 or 2; and
m is 3 or 4;
or pharmaceutically acceptable salts thereof in an amount of from about 500 mg to about 1.5 gm per day.

2. The method of claim 1, wherein the disease is an acute form of neurodegeneration.

3. The method of claim 2, wherein the acute form of neurodegeneration is caused by stroke or brain trauma.

4. The method of claim 1, wherein the disease is a chronic form of neurodegeneration.

5. The method of claim 4, wherein the disease is Alzheimer's, Parkinson's, Huntington's, amyotrophic lateral sclerosis or neurodegeneration associated with bacterial or viral infection.

6. The method of claim 1, comprising administering a compound of formula I selected from the group consisting of:

[4-[3-[4-(4-Fluoro-phenyl)-3,6-dihydro-2H-pyridin-1-yl]-2-hydroxy-propoxy]-phenyl]-urea, N-[4-[3-[4-(4-Fluoro-phenyl)-3,6-dihydro-2H-pyridin-1-yl]-propoxy]-phenyl]-methanesulfonamide hydrochloride (1:1), N-[4-[3-[4-(4-Fluoro-phenyl)-3,6-dihydro-2H-pyridin-1-yl]-2-hydroxy-propoxy]-phenyl]-methanesulfonamide,

[4-[3-[4-(4-Fluoro-phenyl)-3,6-dihydro-2H-pyridin-1-yl]-2-hydroxy-propoxy]-phenyl]-carbamic acid ethyl ester, N-[4-[3-[4-(4-chloro-phenyl)-3,6-dihydro-2H-pyridin-1-yl]-propoxy]-phenyl]-acetamide and N-[4-[2-[4-(4-Fluoro-phenyl)-3,6-dihydro-2H-pyridin-1-yl]-ethoxy]-phenyl]-methanesulfonamide.

7. A method for the control or treatment of diseases caused by over activation of NMDA receptor subtypes comprising administering to a host in need of such control or treatment, a compound of the formula

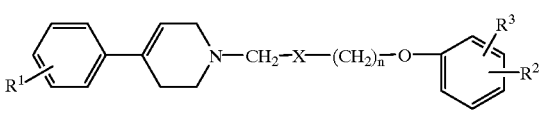

wherein
$R^1$ is hydrogen, halogen, lower alkyl or lower alkoxy;
$R^2$ is hydrogen;
$R^3$ is hydrogen, amino, ureido, lower alkylcarbonyl, lower alkyl-sulfonylamino, lower alkylcarbamoyl, carbamoyl, lower alkyloxycarbamoyl, lower alkylamino or
$R^2$ and $R^3$ taken together are —$(CH_2)_m$—;
X is methylene, hydroxymethylene, lower alkoxymethylene or carbonyl;
n is 0, 1 or 2; and
m is 3 or 4;
or pharmaceutically acceptable salts thereof in an amount of from about 5 mg to about 1000 mg per day.

8. The method of claim 7, wherein the disease is an acute form of neurodegeneration.

9. The method of claim 8, wherein the acute form of neurodegeneration is caused by stroke or brain trauma.

10. The method of claim 7, wherein the disease is a chronic form of neurodegeneration.

11. The method of claim 10, wherein disease is Alzheimer's, Parkinson's, Huntington's, amyotrophic lateral sclerosis or neurodegeneration associated with bacterial or viral infection.

12. The method of claim 7, comprising administering a compound of formula I selected from the group consisting of:

[4-[3-[4-(4-Fluoro-phenyl)-3,6-dihydro-2H-pyrdin-1-yl]-2-hydroxy-propoxy]-phenyl]-urea, N-[4-[3-[4-(4-Fluoro-phenyl)-3,6-dihydro-2H-pyridin-1-yl]-propoxy]-phenyl]-methanesulfonamide hydrochloride (1:1), N-[4-[3-[4-(4-Fluoro-phenyl)-3,6-dihydro-2H-pyridin-1-yl]-2-hydroxy-propoxy]-phenyl]-methanesulfonamide,

[4-[3-[4-(4-(Fluoro-phenyl)-3,6-dihydro-2H-pyridin-1-yl]-2-hydroxy-propoxy]-phenyl]-carbamic acid ethyl ester, N-[4-[3-[4-(4-chloro-phenyl)-3,6-dihydro-2H-pyridin-1-yl]-propoxy]-phenyl]-acetamide and N-[4-[2-[4-(4-Fluoro-phenyl)-3,6-dihydro-2H-pyridin-1-yl]-2-ethoxy]-phenyl]-methanesulfonamide.

* * * * *